United States Patent
Blackburn et al.

(10) Patent No.: US 9,063,146 B2
(45) Date of Patent: Jun. 23, 2015

(54) SYSTEM AND METHOD FOR DISPLAY TYPE DETECTION OF A HANDHELD MEDICAL DEVICE

(71) Applicant: Roche Diagnostics Operations, Inc., Indianapolis, IN (US)

(72) Inventors: Michael J. Blackburn, Indianapolis, IN (US); Nathan E. Manlove, Noblesville, IN (US); Paul S. Rutkowski, Carmel, IN (US)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 57 days.

(21) Appl. No.: 14/062,922

(22) Filed: Oct. 25, 2013

(65) Prior Publication Data

US 2015/0118759 A1 Apr. 30, 2015

(51) Int. Cl.
*G01N 33/66* (2006.01)
*G01N 27/04* (2006.01)

(52) U.S. Cl.
CPC ....... *G01N 33/66* (2013.01); *Y10T 436/144444* (2015.01); *G01N 27/04* (2013.01)

(58) Field of Classification Search
CPC ....... G01N 33/48; G01N 33/50; G01N 33/52; G01N 33/66; G01N 27/00; G01N 27/04; G01N 27/041; Y10T 436/144444
USPC ................ 436/63, 95, 149; 422/82.01, 82.02; 435/14; 600/347, 365
See application file for complete search history.

(56) References Cited

U.S. PATENT DOCUMENTS

| | | |
|---|---|---|
| 5,469,070 A | 11/1995 | Koluvek |
| 5,767,454 A | 6/1998 | Goodwin, III |
| 5,783,926 A | 7/1998 | Moon et al. |
| 7,999,674 B2 | 8/2011 | Kamen |
| 8,894,933 B2 * | 11/2014 | Cadio et al. ................ 422/82.05 |
| 2006/0087327 A1 | 4/2006 | Ueno et al. |
| 2007/0176867 A1 | 8/2007 | Reggiardo et al. |
| 2008/0074136 A1 | 3/2008 | Shiraki et al. |
| 2008/0312584 A1 | 12/2008 | Montgomery et al. |
| 2009/0073098 A1 | 3/2009 | Li |

(Continued)

FOREIGN PATENT DOCUMENTS

| | | |
|---|---|---|
| EP | 2485079 A1 | 8/2012 |
| EP | 2546825 A1 | 1/2013 |

(Continued)

*Primary Examiner* — Maureen Wallenhorst
(74) *Attorney, Agent, or Firm* — Harness, Dickey

(57) ABSTRACT

A device which supports identification of an integrated display and dynamic adjustments to operating parameters thereof includes: a port that receive a test strip having a reaction site for receiving a sample of fluid from a patient, a blood glucose (bG) meter cooperatively operable with a test strip inserted in the port to measure glucose in a sample of fluid on the test strip, and a display device having an electrically resistive component integrated therein and operable to display the glucose measurement in accordance with one or more operating parameters associated with the display device The system also includes a monitoring module electrically connected to the resistive component, wherein the monitoring module determines a type for the display device based on a resistance of the resistive component and a control module that selectively adjusts a given operating parameter of the display device in accordance with the type of display device.

20 Claims, 6 Drawing Sheets

(56) References Cited

U.S. PATENT DOCUMENTS

2010/0204557 A1* 8/2010 Kiaie et al. .................. 600/365
2010/0323431 A1 12/2010 Rutkowski et al.

FOREIGN PATENT DOCUMENTS

| WO | 2011/015353 A2 | 2/2011 |
| WO | 2013/147342 A1 | 10/2013 |

* cited by examiner

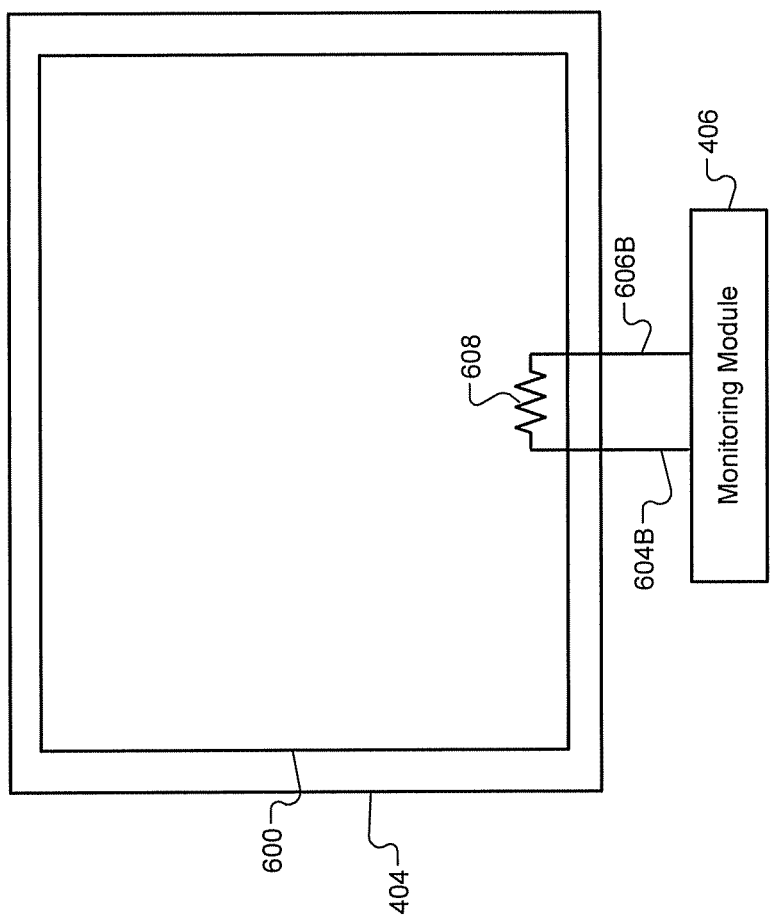

SYSTEM AND METHOD FOR DISPLAY TYPE DETECTION OF A HANDHELD MEDICAL DEVICE

FIELD

The present disclosure relates to a medical device and a system and method for detecting a type of a display integrated with in the medical device, and in particular for adjusting operating parameters of the display device based on the display type.

BACKGROUND

Medical devices are often used as diagnostic devices and/or therapeutic devices in diagnosing and/or treating medical conditions of patients. For example, a blood glucose meter is used as a diagnostic device to measure blood glucose (bG) levels of patients suffering from diabetes. An insulin infusion pump is used as a therapeutic device to administer insulin to patients suffering from diabetes.

In the treatment of the patient, a patient may use a handheld bG meter to measure his or her bG measurements. The patient may rely on these bG measurements to make treatment decisions, e.g., whether or not to take insulin and if so, how much insulin to take. The bG meter includes an integrated display device. The bG meter communicates with the display device in order to display medical data such as a bG measurement or an instruction to provide a blood sample. In order to ensure a consistent perceived appearance of the display device, the display device may be adjusted based on display parameters associated with a display type of the display device. Accordingly, a system and method for detecting the display type of the display device and for adjusting the display parameters of the display device is desired.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A handheld medical device which supports identification of an integrated display and dynamic adjustments to operating parameters thereof includes a port configured to receive a test strip having a reaction site for receiving a sample of fluid from a patient. The system further includes a blood glucose (bG) meter cooperatively operable with a test strip inserted in the port to measure glucose in a sample of fluid residing on the test strip and a display device having an electrically resistive component integrated therein and operable to display the glucose measurement in accordance with one or more operating parameters associated with the display device The system also includes a monitoring module electrically connected to the resistive component, wherein the monitoring module operates to determine a resistance of the electrically resistive component and a type for the display device based on the resistance and a control module in data communication with the display device and the monitoring module, wherein the control module selectively adjusts a given operating parameter of the display device in accordance with the type of display device.

A method for identification of an integrated display and dynamic adjustments to operating parameters thereof, includes: receiving a test strip having a reaction site for receiving a sample of fluid from a patient; measuring glucose in a sample of fluid residing on the test strip; displaying the glucose measurement in accordance with one or more operating parameters associated with a display device; determining a resistance of an electrically resistive component integrated within the display device and a type for the display device based on the resistance; and selectively adjusting a given operating parameter of the display device in accordance with the type of display device.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

FIG. 5B shows an alternative configuration of a monitoring module that determines a type of display device according to the various embodiments of the present disclosure.

Figure 1:
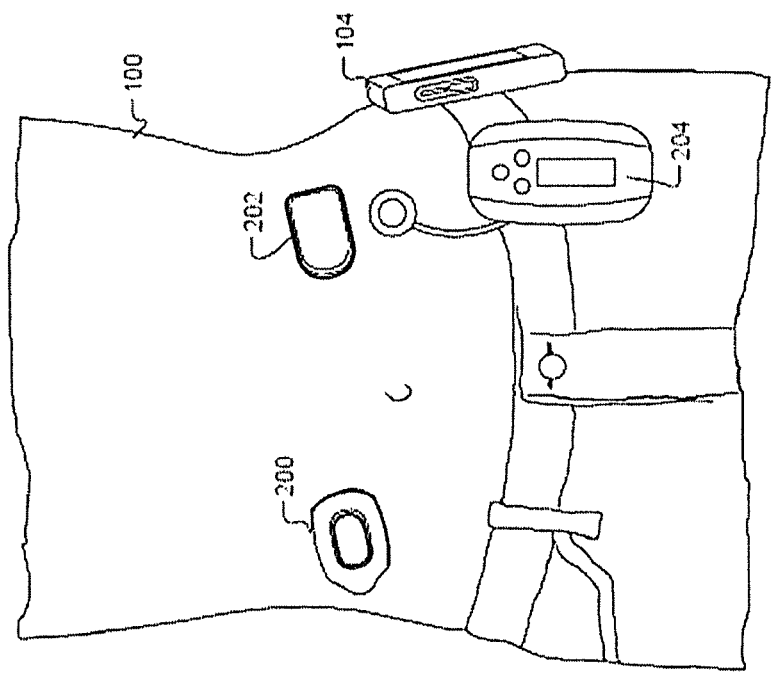
FIG. 1 shows a patient and a treating clinician.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Referring now to FIG. 1, a patient 100 with diabetes and a clinician 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose (bG) measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
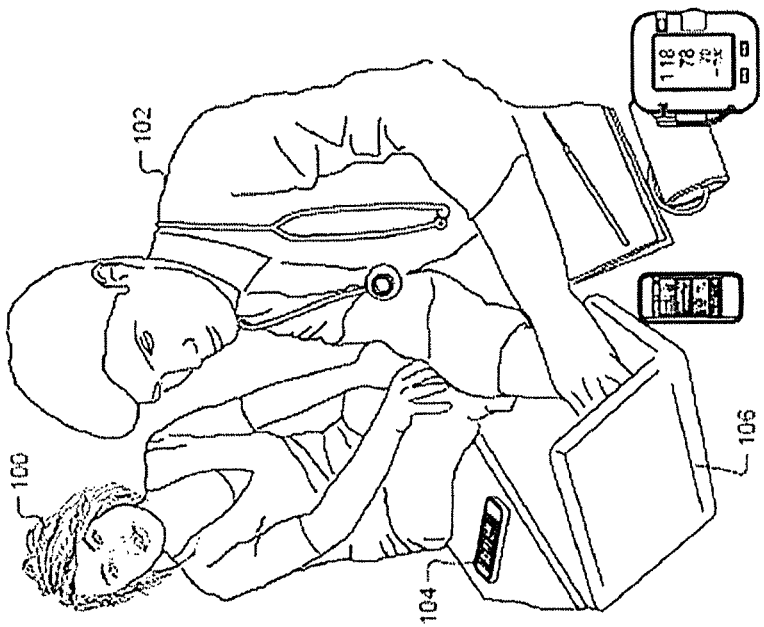
FIG. 2 shows a patient with a continuous glucose monitor (CGM), ambulatory durable insulin infusion pump, ambulatory non-durable insulin infusion pump, and a diabetes manager in accordance with various embodiments of the present disclosure.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
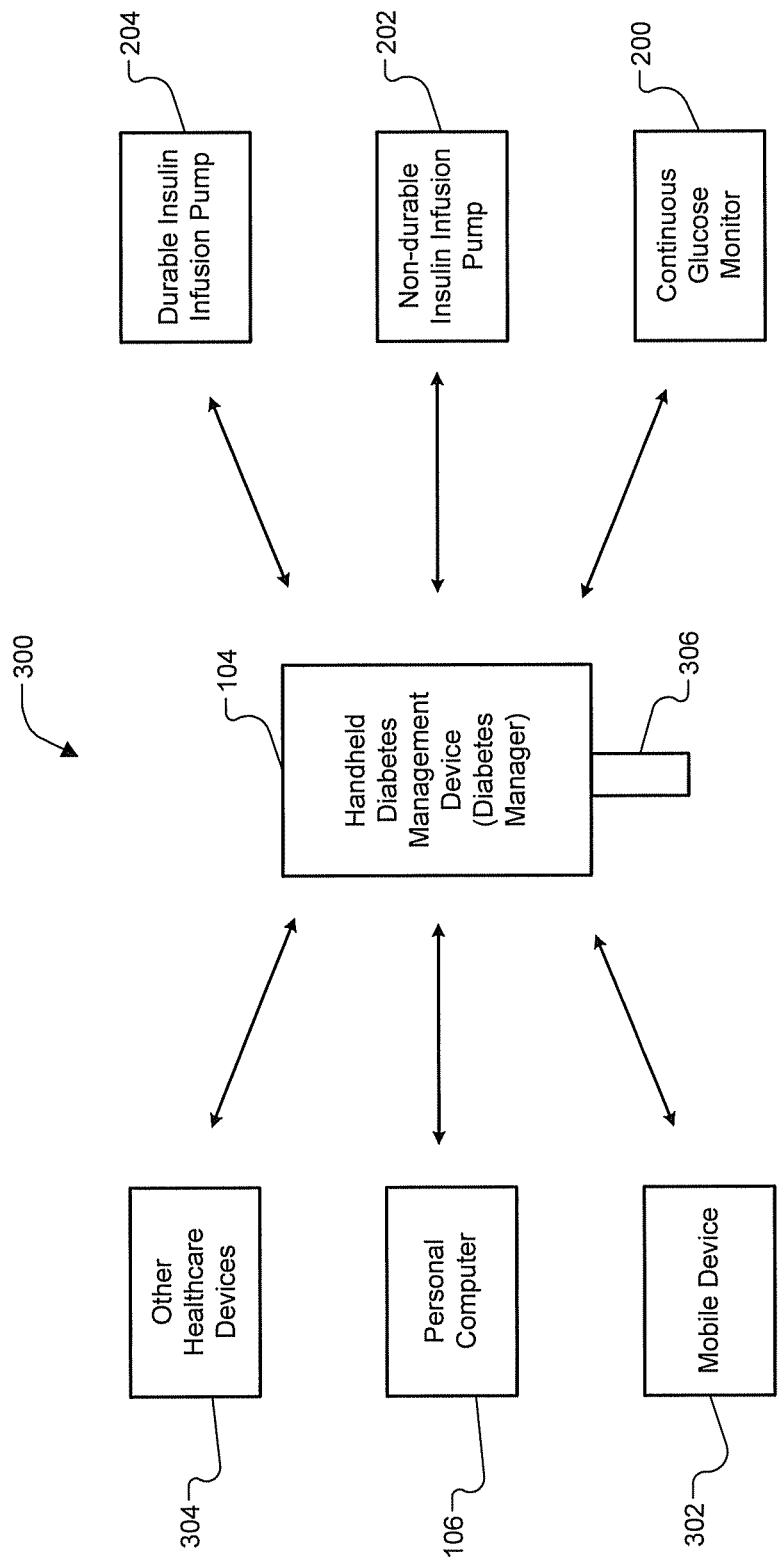
FIG. 3 shows a diabetes care system of systems used by patients and clinicians to manage diabetes in accordance with various embodiments of the present disclosure.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth) and/or wireline interfaces (e.g., USB). Communication protocols used by these devices can include but are not limited to protocols compliant with the IEEE 11073 standard as extended using guidelines provided by Continua® Health Alliance Design Guidelines. Further, healthcare records systems such as Microsoft® HealthVault™ can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using, for example, a proprietary Gazell wireless protocol developed by Nordic Semiconductor, Inc.

Additionally, the diabetes manager 104 includes a blood glucose meter (BGM) and a port that communicates with the BGM (both not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continua® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a PDA, or a pager. The diabetes manager 104 can send messages to an external network through the mobile device 302. The mobile device 302 can transmit messages to the external network based on requests received from the diabetes manager 104.

Figure 4:
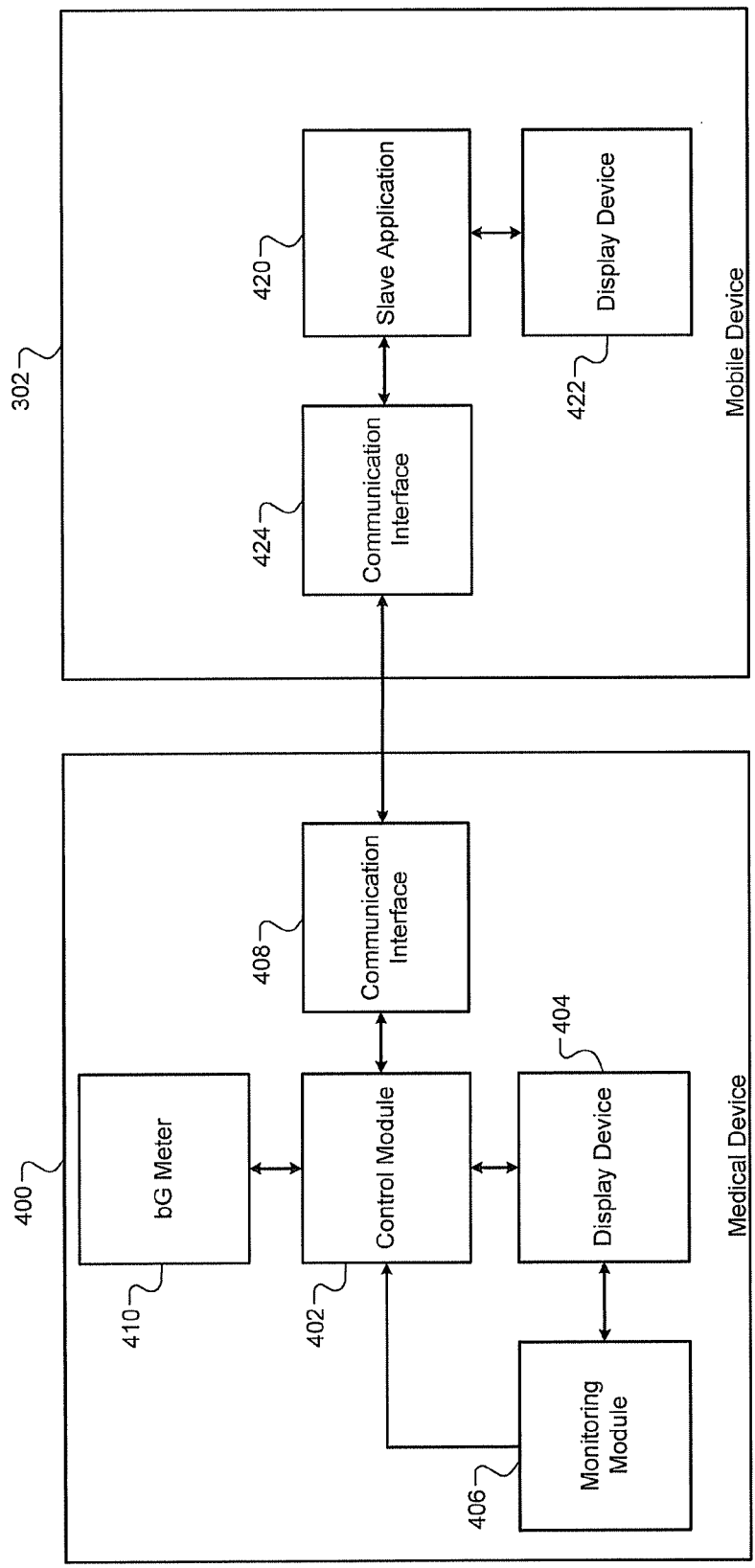
FIG. 4 shows a block diagram illustrating example components of a medical device and a mobile device according to various embodiments of the present disclosure.

Referring now to FIG. 4, a medical device 400 in communication with mobile device 302 is illustrated. For purposes of explanation, it is assumed that the medical device 400 and the mobile device 302 are paired devices, such that communication between the medical device 400 and the mobile device 302 is enabled. In the illustrative example, the medical device 400 is a diabetes manager 104 (as shown FIGS. 1, 2, and 3) and includes a control module 402, a display device 404, a monitoring module 406, a communication interface 408, and a bG meter 410. In the example embodiment, the medical device 400 is configured to determine an electrical resistance of a resistive component integrated within the display device 404 to determine a display type of the display device 404.

The monitoring module 406 communicates the display type to the control module 402. In the illustrative embodiment, the mobile device 302 includes a slave application 420, a display device 422, and a communication interface 424. It is appreciated that the medical device 400 and the mobile device 302 include additional components that are not shown and the components described herein are provided for example and are not intended to be exhaustive.

As mentioned above, in the illustrative example the medical device 400 is a diabetes manager 104. Thus, the medical device 400 includes the bG meter 410. The bG meter 410 receives a bG measurement strip 306 (FIG. 3), which the patient doses with a blood sample, and determines a bG measurement based on blood sample. The bG measurement is provided to the control module 402 for display on the display device 404.

The control module 402 is configured to control the operation of the medical device 400. The control module 402 can determine when a patient is to be prompted to provide a blood sample, perform structured testing, determine any corrective actions that may be taken based on a bG reading, and/or perform any other suitable tasks. Further, the control module 402 is configured to display medical data on the display device 404. In the case of a diabetes manager 104, the control module 402 can provide medical data, e.g., bG measurements determined by the bG meter 410 or instructions to the patient for providing a blood sample, for display by the display device 404.

The display device 404 can be any device capable of electronically displaying data. The display device 404 is integrated within the medical device 400 such that a screen of the display device 404 is located at a front surface of the medical device 400. In some embodiments, the display device 404 is a touchscreen that displays data and can detect the presence of a touch within the display area. In these embodiments, the display device 404 can be a capacitive touchscreen, an infrared touchscreen, resistive touchscreen, or any other type of touchscreen. In other embodiments the display device 404 is an LCD display. The medical device 400 may also include a user interface (not shown) such as a keyboard or physical buttons. The display device 404 may also include a display cache (not shown) which caches information that is to be displayed by the display device 404.

Figure 5A:
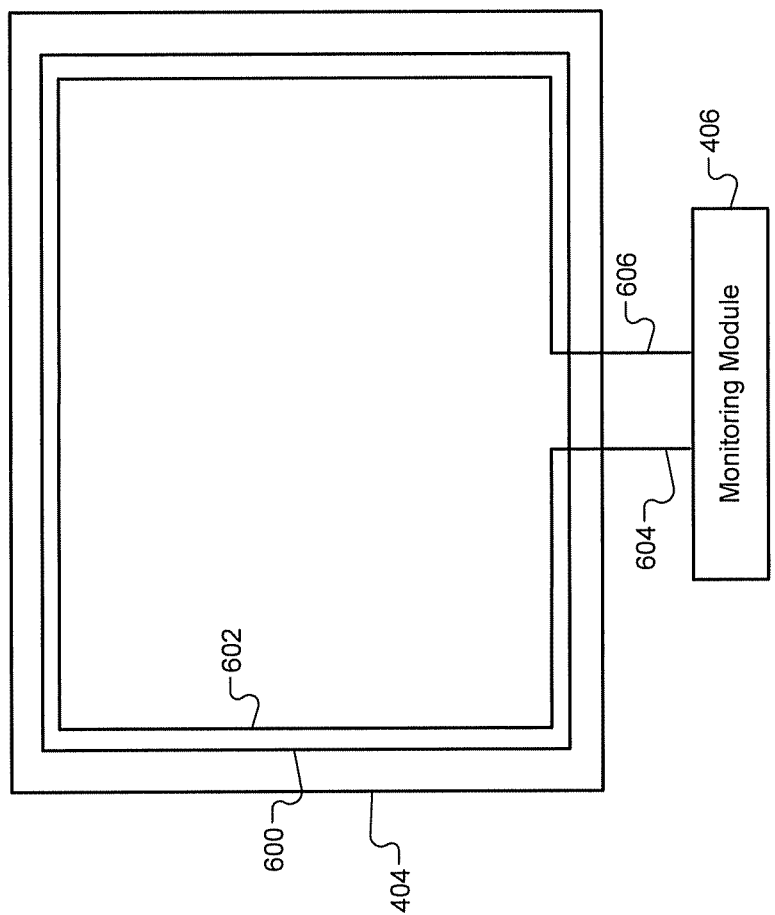
FIG. 5A shows an example configuration of a monitoring module that determines a type of display of a display device according to various embodiments of the present disclosure.

The display device 404 includes an electrically conductive loop 602 as shown in FIG. 5A. In the exemplary embodiment, the conductive loop 602 is integrated along a peripheral edge of a screen 600. The conductive loop 602 may be a thin wire made from indium tin oxide. It should be appreciated that the conductive loop 602 can be made from any other suitable conductive material which can be formed into a thin wire. In the case of an LCD display or a touchscreen display, the conductive loop 602 can be integrated along the peripheral edge of a glass or plastic panel of the screen 600.

The monitoring module 406 is electrically coupled to the conductive loop 602 at a first end 604 of the conductive loop 602 and at a second end 606 of the conductive loop 602. In operation, the monitoring module 406 determines a resistance of the conductive loop 602. For example, the monitoring module 406 applies a predetermined voltage to the conductive loop 602. The monitoring module 406 measures a current flowing from the first end 604 to the second end 606. The monitoring module 406 then determines a resistance value between the first end 604 and the second end 606 based on the applied voltage and the measured current. For example, the monitoring module 406 applies Ohm's Law in order to mathematically determine the resistance between the first end 604 and the second end 606. In other words, the resistance is equal to the applied voltage divided by the measured current.

In the exemplary embodiment, the monitoring module 406 determines the display type of the display device 404. For example, the display device 404 may be one of a plurality of display devices. Each of the plurality of display devices is designed to be integrated into the medical device 400. During assembly of the medical device 400, one of the plurality of display devices is integrated into the medical device 400. Each of the plurality of display devices is configured to meet a predefined display standard. The predefined display standard is designed to ensure each of the plurality of display devices is capable of operably functioning as the display device 404.

Each of the plurality of display devices is manufactured by one of a predetermined plurality of manufacturers. For example, a first display device of the plurality of display devices may be manufactured by a first manufacturer; whereas, a second display device of the plurality of display devices may be manufactured by a second manufacturer. It is understood that a single manufacturer may manufacture one or more of the plurality of display devices. By way of non-limiting example, a third manufacturer may manufacture a third display device, a fourth display device, and a fifth display device. Each of the plurality of display devices has an associated display type. For example, the first display device may be a first display type. Similarly, the second display device may be a second display type. It is understood that the first display type and differ from the second display type. For example, the first display type may include a first color contrast value. Whereas the second display type may include a second color contrast value. It is further understood that that each of display types may be a color display or a black and white display.

Each display type is a type of display device associated with a manufacturer. For example, the first display type may be manufactured by the first manufacture. It is understood that a signal manufacturer may manufacture one or more display types. The display type associated with a particular display device may be identifiable based on a resistance of an electrically conductive loop integrated within the particular display device. Each manufacturer of the plurality of display devices is assigned one or more predetermined conductive loop resistance values.

In one embodiment, the predetermined resistance value is assigned by the manufacturer of the medical device 400. In one example, a first manufacturer is assigned a first conductive loop resistance value and a second conductive loop resistance value. The first manufacturer manufactures a first type of display device. The first type of display device is manufactured to include a first electrically conductive loop. The first manufacturer configures the electrical properties of the first electrically conductive loop to have a resistance equal to the first conductive loop resistance value.

The first manufacturer may also manufacture a second type of display device. The second type of display device is manufactured to include a second electrically conductive loop. The first manufacture configures the electrical properties of the second electrically conductive loop to have resistance equal to the second conductive loop resistance value.

The monitoring module 406 determines the display type of the display device 404 based on a measured resistance of the conductive loop 602. For example, the monitoring module 406 measures the resistance between the first end 604 and the second end 606. The monitoring module 406 compares the measured resistance value to a list of predefined resistances values. For example, the list of predefined resistances may be a look-up table of resistance values. Each predefined resistance value is an entry in the list of predefined resistances. Each entry in the list of predefined resistances may include a plurality of associated fields as will be described in detail below. Each of the predefined resistance values correspond to a display type. The monitoring module 406 determines the display type associated with the measured resistance value. In this way, the monitoring module 406 determines the display type of the display device 404.

In some implementations, the monitoring module 406 determines the display type of the display device 404 when the medical device 400 is powered on. For example, the monitoring module 406 determines the display type as described above each time the medical device 400 is turned on. In another implementation, the monitoring module 406 stores a display type value in an associated memory. When the medical device 400 is powered on, the monitoring module 406 reads the display type value stored in the associated memory in order to determine the display type of the display device 404.

With particular reference to FIG. 5B, an alternative configuration of the display device 404 includes a resistor 608. The resistor 608 may be a passive two terminal resistor or any other suitable electrical resistor. It is further understood that the resistor 608 may be a plurality of resistors electrically coupled to achieve a desired combined resistance. The monitoring module 406 is electrically coupled to the resistor 608 at a first end 604B of the resistor 608 and at a second end 606B of the resistor 608. In operation, the monitoring module 406 determines a resistance of the resistor 608. The monitoring module 406 applies a predetermined voltage to the resistor 608. The monitoring module 406 measures a current flowing from the first end 604B to the second end 606B. The monitoring module 406 then determines a resistance value between the first end 604B and the second end 606B based on the applied voltage and the measured current. For example, the monitoring module 406 applies Ohm's Law in order to mathematically determine the resistance between the first end 604B and the second end 606B. In other words, the resistance is equal to the applied voltage divided by the measured current.

In the exemplary embodiment, the monitoring module 406 determines the display type of the display device 404 as described with respect to FIG. 5A. For example, the display device 404 may be one of the plurality of display devices. Each of the plurality of display devices is designed to be integrated into the medical device 400. During assembly of the medical device 400, one of the plurality of display devices is integrated into the medical device 400. Each of the plurality of display devices is configured to meet a predefined display standard. The predefined display standard is designed to ensure each of the plurality of display devices is capable of operably functioning as the display device 404.

Each of the plurality of display devices is manufactured by one of the predetermined plurality of manufacturers. For example, a first display device of the plurality of display devices may be manufactured by a first manufacturer; whereas, a second display device of the plurality of display devices may be manufactured by a second manufacturer. It is understood that a single manufacturer may manufacture one or more of the plurality of display devices. By way of non-limiting example, a third manufacturer may manufacture a third display device, a fourth display device, and a fifth display device. Each of the plurality of display devices has an associated display type. For example, the first display device may be a first display type. Similarly, the second display device may be a second display type. It is understood that the first display type and differ from the second display type. For example, the first display type may include a first color contrast value. Whereas the second display type may include a second color contrast value. It is further understood that that each of display types may be a color display or a black and white display.

Each display type is a type of display device associated with a manufacturer. For example, the first display type may be manufactured by the first manufacture. It is understood that a signal manufacturer may manufacture one or more display types. The display type associated with a particular display device may be identifiable based on a resistance of resistor integrated within the particular display device. Each manufacturer of the plurality of display devices is assigned one or more predetermined resistance values.

In one embodiment, the predetermined resistance value is assigned by the manufacturer of the medical device 400. In one example, a first manufacturer is assigned a first resistance value and a second resistance value. The first manufacturer manufactures a first type of display device. The first type of display device is manufactured to include a first resistor. The first manufacturer may select the first resistor to have a resistance equal to the first resistance value. Alternatively, the first manufacture may select a plurality of resistors to have a combined resistance equal to the first resistance value.

The first manufacturer may also manufacture a second type of display device. The second type of display device is manufactured to include a second resistor. The first manufacture configures may select the second resistor to have resistance equal to the second resistance value. Alternatively, the first manufacture may select a plurality of resistors to have a combined resistance equal to the second resistance value.

The monitoring module 406 determines the display type of the display device 404 based on a measured resistance of the resistor 608. For example, the monitoring module 406 measures the resistance between the first end 604B and the second end 606B. The monitoring module 406 compares the measured resistance value to a list of predefined resistances values. For example, the list of predefined resistances may be a look-up table of resistance values. Each predefined resistance value is an entry in the list of predefined resistances. Each entry in the list of predefined resistances may include a plurality of associated fields as will be described in detail below. Each of the predefined resistance values correspond to a display type. The monitoring module 406 determines the display type associated with the measured resistance value. In this way, the monitoring module 406 determines the display type of the display device 404.

The display device 404 includes dynamically adjustable operating parameters. For example, brightness, contrast, gray scale, flicker, and tint may be adjusted in order to change the perceived appearance of the display device 404. It is understood that while only a limited number of adjustable operating parameters of the display device 404 are described, the display device 404 may include any other suitable adjustable operating parameter.

Due to variances in manufacturing processes and materials used to manufacture the plurality of display devices, the dynamically adjustable operating parameters of the display device 404 may be selectively adjusted in order to alter the perceived appearance of the display device 404. In this way, a display device integrated within a first instance of the medical device 400 has a consistent perceived appearance with that of a display device integrated within a second instance of the medical device 400. For example, the monitoring module 406 determines the display type of the display device 404 as previously discussed. Each entry in the list of predefined resistances includes a predefined resistance and an associated display type. For example, a first resistance is associated with a first display type. Each entry in the list of predefined resistances also includes an associated predefined operating parameters values set. For example, the first display type may include a corresponding first predefined operating parameter values set.

The monitoring module 406 determines the predefined operating parameter values corresponding to the display device 404. For example, the measured resistance may be a resistance equivalent to the first resistance. The first resistance corresponds to the first display type. The first display type corresponds to the first predefined operating parameter values set. The first predefined operating parameter values set may include a brightness value, a contrast value, a gray scale value, and a tint value. It is understood that the first predefined operating parameter values set may include any alternative or additional suitable parameter value to those described herein.

The monitoring module 406 communicates the predefined operating parameter values set associated with the display device 404 to the control module 402. The control module 402 selectively adjusts the dynamically adjustable operating parameters of the display device 404 based on the predefined operating parameter values set. For example, the monitoring module 406 communicates the first predefined operating parameter values set to the control module 402. The control module 402 adjusts the dynamically adjustable operating parameters of the display device 404 based on the first predefined operating parameter values set. For example only, the control module 402 sets a brightness of the display device 404 equal to the brightness value of the first predefined operating parameter values set.

In one embodiment, the monitoring module 406 determines whether to adjust the dynamically adjustable operating parameters of the display device 404. For example, the monitoring module 406 determines whether the operating parameters of the display device 404 are set to a default value. As described above, the monitoring module 406 determines the display type of the display device 404. Each of the entries in the list of predefined resistances may also include an associated default operating parameter values set. For example, the first resistance corresponds to the first display type. The first display type is associated with the first predetermined operating parameters values set. Further, the first display type is associated with a first operating default parameter values set. The first default parameter values set may include a default brightness value, a default contrast value, a default gray scale value, and a default tint value. It is understood that the first default operating parameter values set may include any alternative or additional suitable parameter value to those described herein.

The monitoring module 406 determines a current operating parameter values set of the display device 404. For example, the monitoring module 406 determines a current brightness value, a current gray scale value, a current contrast value, and a current tint value of the display device 404. The monitoring module 406 then compares each of the determined current operating parameter values with each of the first default operating parameter values. When the monitoring module 406 determines the current operating parameter values are the same as the first default operating parameter values, the monitoring module 406 communicates the first predefined operating parameter values set to the control module 402. The control module 402 then adjusts the dynamically adjustable operating parameters of the display device 404 to be equal to the first predefined operating parameter values.

When the monitoring module 406 determines the current operating parameter values are not the same as the first default operating parameter values, the monitoring module 406 then compares each of the determined current operating parameter values with each of the first predefined operating parameter values. When the monitoring module 406 determines the current operating parameter values are not the same as the first predefined operating parameter values, the monitoring module communicates the first predefined operating parameter values set to the control module 402. The control module 402 then adjusts the dynamically adjustable operating parameters of the display device 404 to be equal to the first predefined operating parameter values.

Conversely, when the monitoring module 406 determines the current operating parameter values are the same as the first predefined operating parameter values, the monitoring module does not communicates the first predefined operating parameter values set to the control module 402. In other words, the dynamically adjustable operating parameters of the display device 404 are adjusted to be equal to the first predefined operating parameter values set, and therefore, the control module 402 does not adjust the dynamically adjustable operating parameters of the display device 404.

In another embodiment, the monitoring module 406 determines whether a user of the medical device 400 has adjusted one or more dynamically adjustable operating parameters of the display device 404. The list of predefined resistances may include a user defined operating parameter values set. The user defined operating parameter values set may be dynamically adjustable based on input from a user.

For example, if the user of the medical device 400 adjusts a brightness value of the display device 404, a brightness value of the user defined operating parameter values set may be dynamically adjusted to be equal to the brightness value set by the user. In the example embodiment, the monitoring module 406 compares each of the determined current operating parameter values with each of the user defined operating parameter values. When the monitoring module 406 determines the current operating parameter values are not the same as the user defined operating parameter values, the monitoring module communicates the user defined operating parameter values set to the control module 402. The control module 402 then adjusts the dynamically adjustable operating parameters of the display device 404 to be equal to the user defined operating parameter values set.

Conversely, when the monitoring module 406 determines the current operating parameter values are the same as the user defined operating parameter values, the monitoring module does not communicates the user defined operating parameter values set to the control module 402. In other words, the dynamically adjustable operating parameters of the display device 404 are adjusted to be equal to the user defined operating parameter values set, and therefore, the control module 402 does not adjust the dynamically adjustable operating parameter of the display device 404.

In another embodiment, the monitoring module 406 determines whether to adjust the dynamically adjustable operating parameters of the display device 400 based on whether the medical device 400 is being started for the first time. For example, the medical device 400 may set a startup value within an associated memory when the medical device 400 is initially started. The startup value may be set to a factory setting. For example, the startup value may be set to 0 when the medical device 400 is assembled. The medical device 400 may be configured to set the startup value to 1 when the medical device 400 is initially started. The monitoring module 406 determines whether to adjust the dynamically adjustable operating parameters of the display device 400 based on the startup value. For example, when the startup value is 0 the monitoring module 406 determines to adjust the dynamically adjustable operating parameters. The monitoring module 406 then determines the device type associated with the display device 404 as described above. Conversely, when the startup value is 1, the monitoring module 406 determines not to adjust the dynamically adjustable operating parameters.

As will be discussed in greater detail below, the mobile device 302 is configured to act as a slave device of the medical device 400. By way of non-limiting example only, the control module 402 is configured to provide commands to the mobile device 302 to display the medical data. The commands can include the medical data which is to be displayed by the mobile device 302. Furthermore, the control module 402 can provide a command to the mobile device 302 to display a graphical user interface (GUI) to the patient such that the patient can interact with medical device 400 via a user interface of the mobile device 302.

In the illustrated example, the communication interface 408 is configured to effectuate communication with one or more other devices, including the mobile device 302. The communication interface 408 can implement any suitable communication protocol. For example, the communication interface 408 can be a Bluetooth® transceiver, an 802.11 transceiver, an infrared transceiver, or any other suitable transceiver. Alternatively, the communication interface 408 can be a wired communication interface such as a USB interface. In the illustrative embodiment, the control module 402 provides commands to the mobile device 302 via the communication interface 408.

The mobile device 302 can be any suitable mobile device, including but not limited to a mobile telephone, a tablet computing device, a personal digital assistant (PDA). As should be appreciated the display device 422 of the mobile device 302 can be any suitable display, including but not limited to a touchscreen or an LCD display.

The mobile device 302 receives commands from the medical device 400 via the communication interface 424 of the mobile device 302. As should be appreciated, mobile devices 302 are typically configured to support numerous different communication protocols. Thus, the communication interface 424 can include a Bluetooth® transceiver, an 802.11 transceiver, an infrared transceiver, and/or any other suitable transceiver. Alternatively, the communication interface 424 can be a wired communication interface such as a USB interface. The communication interface 424 receives commands from the medical device 400 and provides the commands to the slave application 420.

In an exemplary embodiment, the slave application 420 is an application that is executed by one or more processors (not shown) on the mobile device 302. The slave application 420 can be downloaded to and/or installed on the mobile device 302 by the patient. The slave application 420 can be provided by the manufacturer of the mobile device 302 or a third-party. In some embodiments, the slave application 420 may execute as a background process. The slave application 420 may be automatically launched or a visual notification may be displayed to the patient on the display device 422 of the mobile device 302 instructing the patient to launch the slave application 420. Alternatively, the operating system of the mobile device 302 may be configured to receive the notification from the medical device 400 and may automatically launch the slave application 420 upon receiving the notification or may provide the visual notification to the patient instructing the patient to launch the slave application 420.

Once the slave application 420 is launched, the mobile device 302 can be said to be operating in a slave mode, such that the slave application 420 is controlled at least in part by the medical device 400. Thus, the slave application 420 receives commands from the medical device 400 and performs actions defined in the commands. Thus, the slave application 420 can include one or more GUI screens that can be displayed by the display device 422 of the mobile device 302. For example, in some embodiments the slave application 420 can display a GUI screen that replicates a GUI displayed by the display device 404 of the medical device 400. In these embodiments, the slave application may receive a command to display a GUI screen. In response, the slave application 420 displays the GUI screen on the display device 422 of the mobile device 302.

As was discussed, the medical device 400 provides commands to the slave application 420 to display medical data. In some embodiments, the commands can include the type of medical data that is to be displayed and/or the medical data to be displayed. For example, if the medical device 400 provides a command to display a bG measurement, the command may include the value of the bG measurement as well as an indicator that the medical data is a bG measurement to be displayed. In response to the command, the slave application 420 can display a screen for displaying bG measurement values on the display device 422 and can display the received bG measurement value therein.

In another example, the medical device 400 may provide a command to the slave application 420 to display an instruction to the patient to provide a blood sample. In this example, the command may include the instruction to be displayed as well as an indicator that the medical data is an instruction to provide a blood sample. In response to the command, the slave application 420 can display a GUI screen that includes the instruction to provide a blood sample on the display device 422 of the mobile device 302. It should be appreciated that an instruction to provide a blood sample includes any technique for collecting a blood sample, including but not limited to, prompting the patient to insert a blood strip and to dose the blood strip with the blood sample after insertion, and prompting the patient to insert an already dosed blood sample. Furthermore, in some embodiments the displayed GUI screen may include a visual button where the patient can verify that the patient has provided the blood sample, e.g., the patient has inserted a blood glucose measurement strip 306 in the bG meter 410. If the patient presses the visual button, the slave application 420 can transmit a verification indicating that the patient has provided the blood sample to the medical device 400 via the communication interface 424.

The foregoing examples are provided to illustrate the types of medical data that the slave application 420 can display on the display device 422 of the mobile device 302 and are not intended to be limiting. It should be appreciated that the slave application 420 can be configured to display other types of medical data depending on the type of medical device 400. For instance, if the medical device 400 is a blood pressure machine the medical data that is displayed may relate to a blood pressure measurement. Furthermore, the mobile device 302 may receive commands from the medical device 400 to display additional information, such as an instruction to contact the medical device 400 manufacturer and a phone number of the medical device 400 manufacturer. In these embodiments, the patient may call the medical device 400 manufacturer to quickly obtain a replacement medical device 400 or a replacement part.

Further, it is appreciated that while FIG. 4 depicts a mobile device 302, the slave application 420 can be implemented on any suitable device that can execute the slave application 420 and has a display device 422 and a communication interface 424, such that the medical device 400 can be paired with the device executing the slave application 420. For example, the slave application 420 may be executed by a personal computer or a television.

Figure 6:
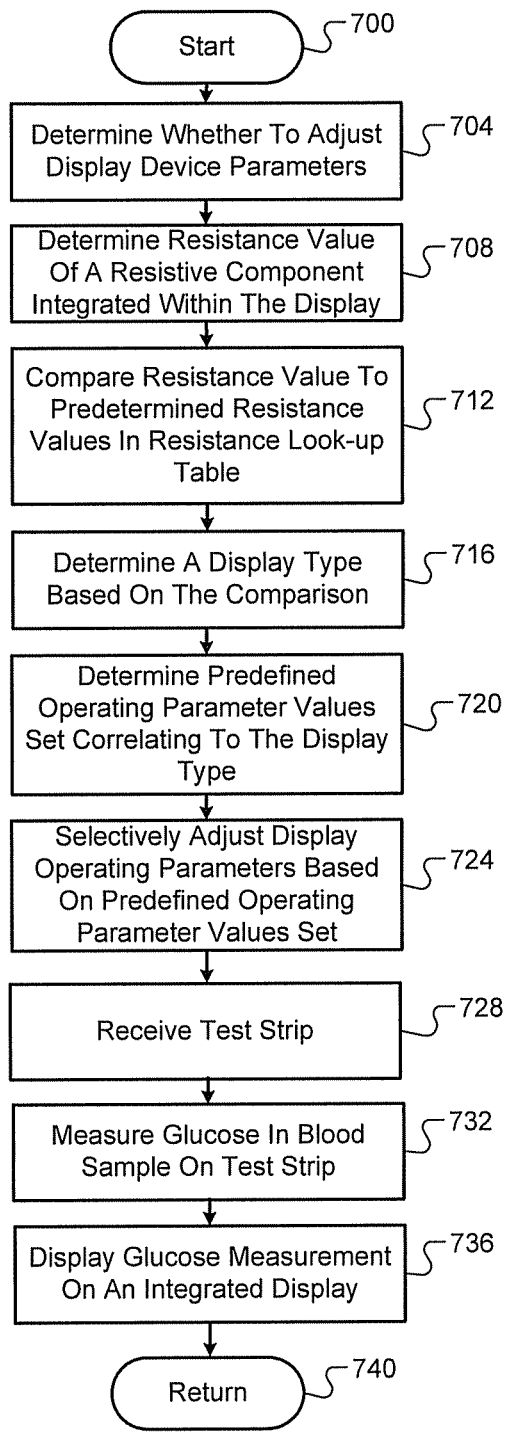
FIG. 6 shows a flow chart illustrating an exemplary method for dynamically adjusting an integrated display according to various embodiments of the present disclosure.

With particular reference to FIG. 6, a flow diagram depicting an example method for determining a display type of the display device 404 begins at 700. At 704, the method 700 determines whether to adjust the dynamically adjustable parameters of the display device 404. In one embodiment, the monitoring module 406 determines whether to adjust the dynamically adjustable operating parameters of the display device 404 based on the startup value as described above. For example, when the startup value is 0, the monitoring module 406 determines the medical device 400 is being started for the first time. When the medical device 400 is started for the first time, the monitoring module 406 determines to adjust the dynamically adjustable operating parameters of the display device 404. At 708, the method 700 determines a resistance value of a resistive component integrated within the display device 404. For example, the monitoring module 406 determines a resistance between the first end 604 and the second end 606.

At 712, the monitoring module 406 compares the measured resistance value with a look-up table of predetermined resistance values. At 716, the monitoring module 406 determines a display type of the display device 404. The monitoring module 406 determines a predetermine resistance value corresponding to the measured resistance value. The predetermined resistance value is associated with a first device type. The first device type corresponds to the device type of the display device 404. At 720, the method 700 determines a predefined operating parameter values set associated with the display type. For example, each of the predetermined resistance values has an associated device type, as described above. The associated device type has an associated predefined operating parameter values set. The monitoring module 406 determines the predefined operating parameter values set associated with the first display type. At 724, the control module 402 selectively adjusts dynamically adjustable operating parameters of the display device 404 based on the predefined operating parameter values set. At 728, the method 700 receives a test strip. The test strip includes a blood sample from a patient. The patient may insert the test strip into a port integrated within the medical device 400. The port is arranged to receive the test strip and the blood sample from the patient. At 732, the method 700 measures a glucose value present in the blood sample included with the test strip. At 736, the method 700 displays the glucose measurement on the display device 404. The method 700 ends at 740.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A handheld medical device which supports identification of an integrated display and dynamic adjustments to operating parameters thereof, comprising:
a port configured to receive a test strip having a reaction site for receiving a sample of fluid from a patient;
a blood glucose (bG) meter cooperatively operable with a test strip inserted in the port to measure glucose in a sample of fluid residing on the test strip;
a display device having an electrically resistive component integrated therein and operable to display the glucose measurement in accordance with one or more operating parameters associated with the display device;
a monitoring module electrically connected to the resistive component, wherein the monitoring module operates to determine a resistance of the electrically resistive component and a type for the display device based on the resistance; and
a control module in data communication with the display device and the monitoring module, wherein the control module selectively adjusts a given operating parameter of the display device in accordance with the type of display device.

2. The handheld medical device of claim 1 wherein the monitoring module compares the determined resistance to a predefined resistance.

3. The handheld medical device of claim 2 wherein the type for the display device corresponds to the predefined resistance.

4. The handheld medical device of claim 1 wherein the type for the display device corresponds to a plurality of predefined operating parameter values.

5. The handheld medical device of claim 4 wherein the control module selectively adjusts a value of the given operating parameter of the display device to be substantially equal to at least one value of the plurality of predefined operating parameter values.

6. The handheld medical device of claim 1 wherein the electrically resistive component includes an electrically conductive loop comprising a wire of an electrically conductive material.

7. The handheld medical device of claim 6 wherein the electrically conductive material is comprised of indium tin oxide.

8. The handheld medical device of claim 1 wherein the electrically resistive component includes a resistor.

9. The handheld medical device of claim 1 wherein the electrically resistive component includes a first end and a second end.

10. The handheld medical device of claim 9 wherein the monitoring module operates to determine the resistance between the first end of the electrically resistive component and the second end of the electrically resistive component.

11. A method for identification of an integrated display and dynamic adjustments to operating parameters thereof, comprising:
- receiving a test strip having a reaction site for receiving a sample of fluid from a patient;
- measuring glucose in a sample of fluid residing on the test strip;
- displaying the glucose measurement in accordance with one or more operating parameters associated with a display device;
- determining a resistance of an electrically resistive component integrated within the display device and a type for the display device based on the resistance; and
- selectively adjusting a given operating parameter of the display device in accordance with the type of display device.

12. The method of claim 11 further comprising comparing the determined resistance to a predefined resistance.

13. The method of claim 12 wherein the type for the display device corresponds to the predefined resistance.

14. The method of claim 11 wherein the type for the display device corresponds to a plurality of predefined operating parameter values.

15. The method of claim 14 further comprising selectively adjusting a value of the given operating parameter of the display device to be substantially equal to at least one value of the plurality of predefined operating parameter values.

16. The method of claim 11 wherein the electrically resistive component includes an electrically conductive loop comprising a wire of an electrically conductive material.

17. The method of claim 11 wherein the electrically resistive component includes a resistor.

18. The method of claim 11 wherein the electrically resistive component includes a first end and a second end.

19. The method of claim 18 further comprising determining the resistance between the first end of the electrically resistive component and the second end of the electrically resistive component.

20. A handheld medical device which supports identification of an integrated display and dynamic adjustments to operating parameters thereof, comprising:
- a port configured to receive a test strip having a reaction site for receiving a sample of fluid from a patient;
- a blood glucose (bG) meter cooperatively operable with a test strip inserted in the port to measure glucose in a sample of fluid residing on the test strip;
- a display device having a resistor integrated therein and operable to display the glucose measurement in accordance with one or more operating parameters associated with the display device;
- a monitoring module electrically connected to a first end of the resistor and electrically connected to a second end of the resistor, wherein the monitoring module operates to determine a resistance between the first end of the resistor and the second end of the resistor and a type for the display device based on the resistance; and
- a control module in data communication with the display device and the monitoring module, wherein the control module selectively adjusts a given operating parameter of the display device in accordance with the type of display device.

* * * * *